United States Patent [19]

Beck et al.

[11] Patent Number: 5,569,805
[45] Date of Patent: Oct. 29, 1996

[54] CATALYTIC CONVERSION OF AROMATIC COMPOUNDS

[75] Inventors: Jeffrey S. Beck, Princeton, N.J.; Ernest W. Valyocsik, Yardley, Pa.; Chaya R. Venkat, Princeton, N.J.

[73] Assignee: Mobil Oil Corporation, Fairfax, Va.

[21] Appl. No.: 441,502

[22] Filed: May 15, 1995

Related U.S. Application Data

[63] Continuation-in-part of Ser. No. 205,437, Mar. 4, 1994, Pat. No. 5,437,855, which is a continuation-in-part of Ser. No. 137,705, Oct. 18, 1993, abandoned.

[51] Int. Cl.$^6$ .................... C07C 2/66; C07C 5/22
[52] U.S. Cl. .................. 585/446; 585/467; 585/470; 585/475; 585/477; 585/481
[58] Field of Search .................... 585/446, 467, 585/470, 475, 477, 481

[56] References Cited

U.S. PATENT DOCUMENTS

| | | | |
|---|---|---|---|
| 2,904,607 | 9/1959 | Mattox et al. | 260/671 |
| 3,126,422 | 3/1964 | Planchard | 260/671 |
| 3,413,374 | 11/1968 | Sato et al. | 260/672 |
| 3,598,878 | 8/1971 | Kovach et al. | 260/672 |
| 3,598,879 | 8/1971 | Kmecak et al. | 260/672 |
| 3,607,961 | 9/1971 | Kovach | 260/672 R |
| 3,751,504 | 8/1973 | Keown et al. | 260/672 T |
| 3,751,506 | 8/1973 | Burress | 260/671 R |
| 3,962,364 | 6/1976 | Young | 260/671 C |
| 3,965,120 | 6/1977 | Chu | 260/671 M |
| 3,965,207 | 6/1976 | Weinstein | 260/671 M |
| 3,965,208 | 6/1976 | Butter et al. | 260/671 M |
| 3,965,209 | 6/1976 | Butter et al. | 260/671 M |
| 4,007,231 | 2/1977 | Butter | 260/672 T |
| 4,100,214 | 7/1978 | Dwyer | 260/668 A |
| 4,117,026 | 9/1978 | Haag et al. | 260/671 R |
| 4,127,616 | 11/1978 | Rodewald | 260/671 R |
| 4,380,685 | 4/1983 | Chu | 585/466 |
| 4,665,255 | 5/1987 | Chang et al. | 585/467 |
| 4,954,663 | 9/1990 | Marler et al. | 568/791 |
| 4,962,256 | 10/1990 | Le et al. | 585/467 |
| 4,962,257 | 10/1990 | Absil et al. | 585/475 |
| 4,992,606 | 2/1991 | Kushernick et al. | 585/467 |
| 5,001,295 | 3/1991 | Angevine et al. | 585/467 |
| 5,215,648 | 6/1993 | Zones et al. | 585/481 |
| 5,243,117 | 9/1993 | Chang et al. | 585/467 |
| 5,258,565 | 11/1993 | Kresge et al. | 585/467 |
| 5,300,210 | 4/1994 | Zones et al. | 585/481 |
| 5,349,113 | 9/1994 | Chang et al. | 585/477 |
| 5,365,000 | 11/1994 | Kresge et al. | 585/446 |
| 5,367,099 | 11/1994 | Beck et al. | 585/470 |
| 5,371,310 | 12/1994 | Bennett et al. | 585/446 |
| 5,382,737 | 1/1995 | Beck et al. | 585/470 |
| 5,406,015 | 4/1995 | Beck et al. | 585/470 |
| 5,437,855 | 8/1995 | Valyocsik | 502/62 |

OTHER PUBLICATIONS

Grandio, P. et al., "AP-catalyst processes make aromatics at low temperatures", Oil and Gas Journal, 69, No. 48, 62 (Nov., 1971).

*Primary Examiner*—Anthony McFarlane
*Assistant Examiner*—Walter D. Griffin
*Attorney, Agent, or Firm*—Ronald A. Bleeker; Malcolm D. Keen; Peter W. Roberts

[57] ABSTRACT

A process is provided for catalytic conversion of feedstock comprising aromatic compounds to product comprising aromatic compounds which differs from said feedstock. The catalyst required in the process comprises a crystalline material having the structure of MCM-58. Said crystalline material may have been treated with one or more monomeric or polymeric siloxane compounds which decompose to oxide or non-oxide ceramic or solid-state carbon species.

23 Claims, No Drawings

CATALYTIC CONVERSION OF AROMATIC COMPOUNDS

CROSS-REFERENCE TO RELATED APPLICATIONS

This is a continuation-in-part of application Ser. No. 08/205,437, filed Mar. 3, 1994, now U.S. Pat. No. 5,437,855, which is a continuation-in-part of application Ser. No. 08/137,705, filed Oct. 18, 1993, now abandoned.

BACKGROUND OF THE INVENTION

1. Field of the Invention

A process is provided for catalytic conversion of feedstock comprising aromatic compounds to product comprising aromatic compounds which differs from the feedstock. The catalyst required in the process comprises a crystalline material having the structure of MCM-58. Examples of the conversion process include alkylation, disproportionation, isomerization and transalkylation. Said crystalline material may have been treated with one or more monomeric or polymeric siloxane compounds which decompose to oxide or non-oxide ceramic or solid-state carbon species to change selectivity of the reaction, if desired.

2. Description of the Prior Art

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIB element oxide, e.g., $AlO_4$, in which the tetrahedra are cross-linked by the sharing of oxygen atoms whereby the ratio of the total Group IIIB element, e.g., aluminum, and silicon atoms to oxygen atoms is 1:2. The electrovalence of the tetrahedra containing the Group IIIB element, e.g., aluminum, is balanced by the inclusion in the crystal of a cation, e.g., an alkali metal or an alkaline earth metal cation. This can be expressed wherein the ratio of the Group IIIB element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite Z (U.S. Pat. No. 2,882, 243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709, 979); zeolite ZSM-12 (U.S. Pat. No. 3,832,449); zeolite ZSM-20 (U.S. Pat. No. 3,972,983); zeolite ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724; 4,073,865; and 4,104,294 describe crystalline silicate of varying aluminum and metal content.

Disproportionation and alkylation of aromatics are mechanisms for production of para-dialkyl substituted benzenes, such as, for example, para-xylene. The equilibrium composition of xylene product from catalytic processes is approximately 24 wt. % para-isomer, 54 wt. % meta-isomer, and 22 wt. % ortho-isomer. Disproportionation of aromatic hydrocarbons in the presence of zeolite catalysts is described by Grandio et al. in the *Oil and Gas Journal*, 69, 48 (1971). Also U.S. Pat. Nos. 3,126,422; 3,413,374; 3,598,878; 3,598, 879; and 3,607,961 show vapor-phase disproportionation of toluene over various catalysts. Catalysts comprising MCM-22 or PSH-3 are taught for use in U.S. Pat. Nos. 4,954,663; 4,962,256; 4,962,257; 4,992,606; and 5,001,295 for aromatic compound alkylation or disproportionation in general.

U.S. Pat. 4,665,255 teaches conversion, e.g., isomerization, of aromatic compounds over catalyst comprising a porous inorganic crystalline composition having been treated to increase the latice metal in the crystal framework.

U.S. Pat. No. 4,380,685 teaches para-selective alkylation, transalkylation or disproportionation of a substituted aromatic compound to form a dialkylbenzene compound mixture over catalyst comprising zeolite characterized by a constraint index of 1 to 12 and a silica:alumina mole ratio of at least 12:1, the catalyst having thereon incorporated various metals and phosphorus.

Other patents covering alkylation and transalkylation include U.S. Pat. Nos. 4,127,616, 4,361,713, 4,365,104, 4,367,359, 4,370,508 and 4,384,155. Toluene is converted to para-xylene in U.S. Pat. Nos. 3,965,207, 3,965,208, 3,965, 209, 4,001,346, 4,002,698, 4,067,920, 4,100,215 and 4,152, 364, to name a few. Alkylation with olefins is taught, for example, in U.S. Pat. Nos. 3,962,364 and 4,016,218 and toluene is disproportionated in, for example, U.S. Pat. Nos. 4,052,476, 4,007,231, 4,011,276, 4,016,219 and 4,029,716. Isomerization of xylenes is taught in, for example, U.S. Pat. Nos. 4,100,214, 4,101,595, 4,158,676, 4,159,282, 4,351, 979, 4,101,597, 4,159,283, 4,152,363, 4,163,028, 4,188,282 and 4,224,141.

Various methods are known in the art for increasing the para-selectivity of zeolite catalysts. One such method is to modify the catalyst by treatment with a "selectivating agent". For example, U.S. Pat. Nos. 5,173,461; 4,950,835; 4,927,979; 4,477,583; 4,283,306; and 4,060,568 disclose specific methods for contacting a catalyst with a selectivating agent containing silicon ("silicon compound").

U.S. Pat. No. 4,548,914 describes another modification method involving impregnating catalysts with oxides that are difficult to reduce, such as those of magnesium, calcium, and/or phosphorus, followed by treatment with water vapor to improve para-selectivity.

European Pat. No. 296,582 describes the modification of aluminosilicate catalysts by impregnating such catalysts with phosphorus-containing compounds and further modifying these catalysts by incorporating metals such as manganese, cobalt, silicon and Group IIA elements. The patent also describes the modification of zeolites with silicon containing compounds.

U.S. Pat. No. 4,097,543 teaches a process for selective toluene disproportionation to yield increased paraxylene utilizing a specific crystalline zeolite catalyst, e.g., ZSM-5, which has undergone prior treatment to deposit a controlled amount of carbon coke thereon.

In addition to the above patents, U.S. Pat. No. 2,904,607 refers to alkylation of aromatic hydrocarbons with an olefin in the presence of a crystalline metalloaluminosilicate having uniform pore openings of about 6 to 15 Angstrom units. U.S. Pat. No. 3,251,897 describes alkylation of aromatic hydrocarbons in the presence of X- or Y-type crystalline aluminosilicate zeolites, specifically said zeolites wherein the cation is rare earth and/or hydrogen. U.S. Pat. Nos. 3,751,504 and 3,751,506 describe vapor phase alkylation of aromatic hydrocarbons with olefins, e.g., benzene with ethylene, in the presence of, for example, a ZSM-5 zeolite catalyst.

The alkylation of toluene with methanol in the presence of a cation-exchanged zeolite Y has been described by Yashima et al. in the *Journal of Catalysis*, 16, 273–280 (1970). The workers reported selective production of para-xylene over the approximate temperature range of 200° C. to 275° C., with the maximum yield of para-xylene in the mixture of xylenes, i.e., about 50 percent of the xylene product mixture, being observed at 225° C. Higher temperatures were reported to result in an increase in the yield of meta-xylene and a decrease in the production of para- and ortho-xylenes. U.S. Pat. No. 3,965,210 describes alkylation of toluene with methanol in the presence of a crystalline aluminosilicate zeolite, such as ZSM-5, which has been modified by contact with a polymer made up of meta-carborane units connected by siloxane units to selectively yield para-xylene. These latter catalysts have, however, suffered from the serious deficiency of loss of selectivity upon air regeneration. This is attributable to breakage of carbon-silicon bonds upon exposure to the high temperature of regeneration giving rise to isolated clusters of silica on the zeolite surface rather than the extensive surface coverage afforded by the technique described herein.

U.S. Pat. Nos. 4,029,716 and 4,067,920 teach use of a specific catalyst, e.g., ZSM-5 or ZSM-11, which has been pretreated with a particular boron compound to produce paraxylene by alkylating toluene with an olefin. U.S. Pat. No. 4,117,026 teaches selective production of para-dialkyl substituted benzenes over catalyst comprising a large crystal zeolite, e.g., ZSM-5, having certain sorption characteristics.

U.S. Pat. No. 2,722,504 describes a catalyst of an activated oxide such as silica gel having a thin layer of a silicone polymer deposited thereon to increase the organophilic character of the contact surface and, as such, seeks to avoid silica deposition.

Crystalline aluminosilicate zeolites, modified by reaction with an organic substituted silane, have been described in U.S. Pat. Nos. 3,682,996 and 3,698,157. The former of these patents describes, as novel compositions of matter, crystalline aluminosilicate esters made by reacting a crystalline aluminosilicate having an available hydrogen atom with an organic silane having a SiH group. The resulting compositions were disclosed as being catalysts useful for hydrocarbon processes, particularly hydrocracking. In the latter of the above patents, the use of ZSM-5 crystalline aluminosilicate zeolite modified by treatment with an organic-radical substituted silane is described, together with the use of such modified zeolite in chromatographic separation of the compounds in a $C_8$ aromatic feedstock.

U.S. Pat. No. 4,145,315 discloses a method for the production of silica-modified zeolite catalysts which are prepared by contacting the specific zeolite with an organic solvent solution such as hexane, of a silcone fluid, distillation of the hexane, and air calcination of the zeolite residue.

Silica-modified catalysts are shown in U.S. Pat. Nos. 4,379,761; 4,100,219; 4,090,981; and 4,127,616. In each instance the silica modification results from interaction of the zeolite portion of the catalyst with an organic solution comprising a silica source such as a silicone. U.S. Pat. No. 4,465,886 teaches selective conversion of hydrocarbon compounds to product rich in para-dialkyl substituted benzenes over catalyst comprising a zeolite, e.g., ZSM-5, ZSM-5/ZSM-11 intermediate, ZSM-11, ZSM-12, ZSM-23, ZSM-35, ZSM-38, or ZSM-48, having deposited thereon a coating of silica which covers exclusively the external surface of the zeolite.

U.S. Pat. No. 4,088,605 shows altering a crystallization medium to substantially eliminate aluminum during crystallization in order to synthesize a zeolite with a coating of silica.

SUMMARY OF THE INVENTION

In accordance with the present invention, there has been discovered a process for conversion of feedstock comprising aromatic compounds to product comprising aromatic compounds which differs from the feedstock. Conversion mechanisms of the present process include alkylation, disproportionation, isomerization and transalkylation. The catalyst required for the present process comprises a porous crystalline material having the structure of MCM-58, which in the calcined form has a very high acid activity and high sorption capacity. The MCM-58 for use herein may, if desired, be treated with one or more monomeric or polymeric siloxane compounds which decompose to oxide or non-oxide ceramic or solid-state carbon species in order to alter selectivity. If treated, the crystalline MCM-58 employed has an activity, in terms of Alpha Value, of from about 150 to about 1200.

The catalyst comprising MCM-58 has been found to be useful in the production of para-dialkyl substituted benzenes containing alkyl groups of 1 to 4 carbon atoms, such as paraxylene, by conversion of a hydrocarbon precursor such as a mono alkyl-substituted benzene having 1 to 4 carbon atoms in the alkyl substituent or a mixture of such precursor or benzene with an alkylating agent containing from 1 to 4 carbon atoms.

Typical mechanisms of the conversion process are disproportionation of toluene; alkylation of benzene or toluene with an alkylating agent, e.g., methanol; transalkylation of aromatics exemplified by conversion of benzene with diethylbenzene to produce ethylbenzene; and isomerization of aromatics such as diethylbenzene to an equilibrium product mixture.

DESCRIPTION OF SPECIFIC EMBODIMENTS

U.S. applications Ser. Nos. 08/205,437, now U.S. Pat. No. 5,437,855 and 08/137,705, now abandoned, are entirely incorporated herein by reference for definition of MCM-58 and its properties.

The crystalline MCM-58 material for use herein has a composition involving the molar relationship:

$$X_2O_3:(n)YO_2,$$

wherein X is a trivalent element, such as aluminum, boron, iron, indium, and/or gallium, preferably aluminum; Y is a tetravalent element such as silicon, tin, and/or germanium, preferably silicon; and n is from greater than about 10 to about 1000, usually from greater than about 10 to about 400, more usually from about 20 to about 200. In the as-synthesized form, the material has a formula, on an anhydrous basis and in terms of moles of oxides per n moles of $YO_2$, as follows:

$$(0.1-2)M_2O:(0.2-2)R:X_2O_3:nYO_2$$

wherein M is an alkali or alkaline earth metal, and R is an organic moiety. The M and R components are associated with the material as a result of their presence during crystallization, and are easily removed by post-crystallization methods hereinafter more particularly described.

The MCM-58 for use in the invention is thermally stable and in the calcined form exhibits significant hydrocarbon sorption capacity. To the extent desired, the original sodium and/or potassium cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for certain hydrocarbon conversion reactions. These include hydrogen, rare earth metals and metals of Groups IIA, IIIA, IVA, IB, IIB, IIIB, IVB and VIII of the Periodic Table of the Elements.

In the as-synthesized form, the crystalline MCM-58 material for use in the invention appears to be a single crystalline phase. It can be prepared in essentially pure form with little or no detectable impurity crystal phases and has an X-ray diffraction pattern which is distinguished from the patterns of other known as-synthesized or thermally treated crystalline materials by the lines listed in Table I below:

TABLE I

| Interplanar d-Spacing (A) | Relative Intensity, $I/I_o \times 100$ |
|---|---|
| 10.89 ± 0.30 | s-vs |
| 9.19 ± 0.30 | vw |
| 6.55 ± 0.29 | vw-w |
| 5.86 ± 0.28 | vw-w |
| 5.57 ± 0.27 | vw-w |
| 5.43 ± 0.26 | vw-w |
| 4.68 ± 0.25 | vw-m |
| 4.36 ± 0.25 | w-vs |
| 4.17 ± 0.23 | vw-m |
| 4.12 ± 0.23 | vw-s |
| 3.78 ± 0.20 | wv-s |
| 3.61 ± 0.15 | vw-w |
| 3.54 ± 0.15 | vw |
| 3.44 ± 0.15 | vw-m |
| 3.37 ± 0.15 | vw-m |
| 3.06 ± 0.15 | vw-w |
| 2.84 ± 0.15 | vw |
| 2.72 ± 0.13 | vw |
| 2.66 ± 0.12 | vw |

TABLE I-continued

| Interplanar d-Spacing (A) | Relative Intensity, $I/I_o \times 100$ |
|---|---|
| 2.46 ± 0.12 | vw |
| 2.17 ± 0.10 | vw |

These X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's, were calculated in Angstrom units (A), and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (80–100), s=strong (60–80), m=medium (40–60), w=weak (20–40), and vw=very weak (0–20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history.

MCM-58 can be prepared from a reaction mixture containing sources of alkali or alkaline earth metal (M), e.g., sodium and/or potassium, cation, an oxide of trivalent element X, e.g., aluminum and/or boron, an oxide of tetravalent element Y, e.g., silicon, directing agent (R), and water, said reaction mixture having a composition, in terms of mole ratios of oxides, within the following ranges:

| Reactants | Useful | Preferred |
|---|---|---|
| $YO_2/X_2O_3$ | 15 to 1000 | 25 to 500 |
| $H_2O/YO_2$ | 5 to 200 | 20 to 100 |
| $OH^-/YO_2$ | 0 to 3 | 0.10 to 0.50 |
| $M/YO_2$ | 0 to 3 | 0.10 to 2 |
| $R/YO_2$ | 0.02 to 1.0 | 0.10 to 0.50 |

In this synthesis method, the preferred source of $YO_2$ comprises predominately solid $YO_2$, for example at least about 30 wt. % solid $YO_2$. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) is preferred for MCM-58 formation from the above mixture. Preferably, therefore, the $YO_2$, e.g., silica, source contains at least about 30 wt. % solid $YO_2$, e.g., silica, and more preferably at least about 40 wt. % solid $YO_2$, e.g., silica.

The organic directing agent R for use herein above is either the cation benzylquinuclidinium, having a formula $C_{14}H_{20}N^+$ or the cation benzyltropanium, having a formula $C_{15}H_{22}N^+$, and may be represented as follows:

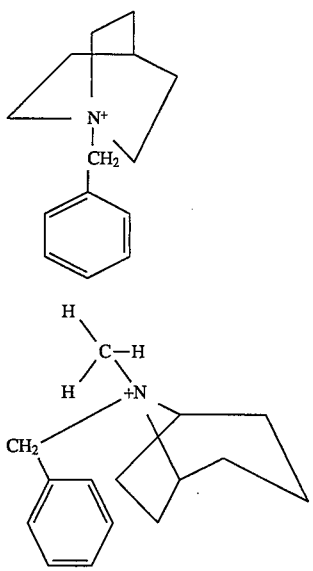

The sources of these organic cations may be, for example, the halide, e.g., chloride or bromide, or hydroxide salt. The source of organic directing agents used in the following examples was synthesized as follows:

(1) Benzylquinuclidinium halide, i.e., bromide, was synthesized by reacting benzylbromide and quinuclidine in absolute ethanol solvent in a flask equipped with a reflux condenser, a thermometer and a stirrer. The flask was charged with 60.0 grams of benzylbromide with 200 ml of absolute ethanol. Then 33.4 grams of quinuclidine dissolved in 300 ml of absolute ethanol was transferred to the flask. Heating and stirring of the flask reaction mixture commenced immediately.

The reaction mixture was refluxed (~70° C.) overnight with stirring before quenching the reaction vessel in a dry ice-acetone bath to −40° C. The cold crystalline product was separated from the solvent, filtered, and washed with anhydrous diethylether on a Büchner funnel. The crystals were dried in an air stream, then chemically analyzed. The benzylquinuclidium bromide product of this example was found to be composed of 56.13 wt. % C, 7.46 wt. % H, 4.66 wt. % N and 28.13 wt. % Br;

(2) Benzyltropanium halide, i.e., bromide, was synthesized by reacting benzylbromide and tropane in absolute ethanol solvent in a flask equipped with a reflux condenser, a thermometer and a stirrer. The flask was charged with 60.0 grams of benzylbromide with 300 ml of absolute ethanol. Then 37.6 grams of tropane dissolved in 300 ml of absolute ethanol was transferred to the flask. Heating and stirring of the flask reaction mixture commenced immediately.

The reaction mixture was refluxed (~70° C.) overnight with stirring before quenching the reaction vessel in a dry ice-acetone bath to −40° C. The cold crystalline product was separated from the solvent, filtered, and washed with anhydrous diethylether on a Büchner funnel. The benzyltropanium bromide product crystals were then dried in an air stream.

Crystallization of the MCM-58 can be carried out at either static or stirred conditions in a suitable reactor vessel, such as for example, polypropylene jars or teflon lined or stainless steel autoclaves. The total useful range of temperatures for crystallization is from about 80° C. to about 250° C. for a time sufficient for crystallization to occur at the temperature used, e.g., from about 12 hours to about 100 days. Thereafter, the crystals are separated from the liquid and recovered.

It should be realized that the reaction mixture components can be supplied by more than one source. The reaction mixture can be prepared either batchwise or continuously. Crystal size and crystallization time of the new crystalline material will vary with the nature of the reaction mixture employed and the crystallization conditions.

Synthesis of MCM-58 crystals may be facilitated by the presence of at least 0.01 percent, preferably 0.10 percent and still more preferably 1 percent, seed crystals (based on total weight) of crystalline product.

The MCM-58 crystals can be shaped into a wide variety of particle sizes for use herein. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

The crystalline material component of the catalyst for use herein is characterized by its unusual structure and its particular activity and sorption properties. Thus, the crystalline material for use herein has (i) the structure of MCM-58; and, if treated with a siloxane compound as indicated, and (ii) an activity, in terms of Alpha Value, of from about 150 to about 1200, preferably from about 200 to about 550.

When Alpha Value is examined, it is noted that the Alpha Value is an approximate indication of the acid catalytic activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 sec$^{-1}$). The Alpha Test is described in U.S. Pat. 3,354,078; in the *Journal of Catalysis*, 4, 527 (1965); 6, 278 (1966); and 61, 395 (1980), each incorporated herein by reference as to that description. The experimental conditions of the test used herein include a constant temperature of 538° C. and a variable flow rate as described in detail in the *Journal of Catalysis*, 61, 395.

Prior to its use as catalyst in the present process, the crystalline material should be subjected to thermal treatment to remove part or all of any organic constituent present therein. This thermal treatment is generally performed by heating at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

The crystalline MCM-58 for use herein may, if desired to alter selectivity, be treated with molecular or polymeric selectivating agent species which alter the diffusion properties of the crystal to be as above defined. This results in enhanced selectivity for the process of the invention. Species used for modification may include, for example, silicon-containing compounds such as monomeric or polymeric siloxanes, other main group species (e.g., those containing Ge, B, P, Mg, and/or Sb) which decompose to oxide or non-oxide ceramics, or solid-state carbon species. U.S. Pat. No. 5,120,692, incorporated herein by reference in its entirety, demonstrates examples of suitable species for use herein.

Useful selectivating agents include siloxanes which can be characterized by the general formula:

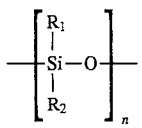

where $R_1$ is hydrogen; halogen; hydroxyl; alkyl or halogenated alkyl of from 1 to 10 carbons; or aryl, halogenated aryl, aralkyl, halogenated aralkyl, alkaryl or halogenated alkaryl of from 6 to 20 carbons. The hydrocarbon substituents generally contain from 1 to 10 carbon atoms, preferably methyl or ethyl groups. $R_2$ is independently selected from the same group as $R_1$, and n is an integer of at least 2 and generally in the range of 3 to 1000. The molecular weight of the silicone compound employed is generally between about 80 and about 20,000 and preferably within the approximate range of 150 to 10,000. Representative silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone and ethylvinyl silicone. The silicone compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used, as may silicones with other functional groups.

Other, more preferred silicon compounds, including silanes, alkoxy silanes, and organoamine silanes, may also be utilized. These useful silicon-containing selectivating agents include silanes characterizable by the general formula:

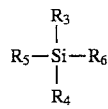

where $R_3$, $R_4$, $R_5$ and $R_6$ are independently selected from the group consisting of hydrogen; hydroxyl; halogen; alkyl of from 1 to 10 carbons; halogenated alkyl of from 1 to 10 carbons; alkoxy; aryl, halogenated aryl, aralkyl, halogenated aralkyl, alkaryl, or halogenated alkaryl of from 6 to 20 carbons; and organoamine groups of from 3 to 9 carbons. Most preferably $R_3$, $R_4$, $R_5$ and $R_6$ are independently selected from the group consisting of —$N(CH_3)_3$, —$N(C_2H_5)_3$ and —$N(C_3H_7)_3$. Mixtures of these compounds may also be used.

Such compounds are preferred because of their amphiphilic character, allowing their dissolution, or at least emulsification, in aqueous carriers, as well as taking advantage of the hydrophobic character of the zeolite on which the silicon compounds are being deposited.

The kinetic diameter of the high efficiency, p-dialkyl aromatic selectivating agent may be larger than the zeolite pore diameter, in order to avoid entry of the selectivating agent into the pore and any concomitant reduction in the internal activity of the catalyst. When a silicon compound is used that is of a size small enough to enter the pores of the catalyst crystal, it is desirable to use the sodium form of the zeolite rather than the hydrogen form.

For use in the present invention, the zeolite, either incorporated with a binder or in unbound form, may be impregnated with the selectivating agent, preferably between about two and about six times. In each phase of the selectivation treatment, the selectivating agent is deposited on the external surface of the catalyst by any suitable method. For example, the selectivating agent may be dissolved in a carrier, mixed with the catalyst and then dried by evaporation or vacuum distillation. This method is termed "impregnation". The molecular sieve may be contacted with the silicon compound at a molecular sieve/silicon compound weight ratio of from about 100/1 to about 1/100.

The silicon compound employed may be in the form of a solution, an emulsion, a liquid or a gas under the conditions of contact with the zeolite. Not wishing to be bound by theory, it is believed that the deposited silicon compound extensively covers, and resides substantially exclusively on, the external surface of the molecular sieve. Examples of methods of depositing silicon on the surface of the zeolite are found in U.S. Pat. Nos. 4,090,981; 4,127,616; 4,465,886; and 4,477,583 to Rodewald, which are incorporated by reference herein. Further examples of silicon deposition on zeolite surfaces are described in Nakajima, H. et al., *Sekiyu Gakkaishi*, 35(2) (1992), and U.S. Pat. No. 4,950,835 to Wang et al.

The catalyst for use in the present invention may be ex situ selectivated by multiple coatings with the high efficiency, para-selectivating agent, each coating followed by calcination, and optionally trim-selectivation with additional high efficiency para-selectivating agent. As used herein, the term "high efficiency, para-selectivating agent" is used to indicate substances which will increase the paraselectivity of a catalytic molecular sieve to the stated levels in alkylbenzene disproportionation while maintaining commercially acceptable levels of alkylbenzene to dialkylbenzene conversion.

Following each deposition of the silicon compound, the catalyst is calcined to decompose the molecular or polymeric species to a solid state species. The catalyst may be calcined at a rate of from about 0.2° C./minute to about 5° C./minute to a temperature greater than 200° C., but below a temperature at which the crystallinity of the zeolite is adversely affected. Generally, such temperature will be below 600° C. Preferably the temperature of calcination is within the approximate range of 350° C. to 550° C. The product is maintained at the calcination temperature usually for 1 to 24 hours, preferably for between 2 and 6 hours.

The catalyst may be calcined in an atmosphere of $N_2$, an oxygen-containing atmosphere, preferably air, an atmosphere of $N_2$ followed by an oxygen-containing atmosphere, or an atmosphere containing a mixture of $N_2$ and air. Calcination should be performed in an atmosphere substantially free of water vapor, to avoid undesirable uncontrolled steaming of the silicon coated catalyst. The catalyst may be calcined once or more than once after each silicon deposition. The various calcinations in any impregnation sequence need not be identical, but may vary with respect to the temperature, the rate of temperature rise, the atmosphere and the duration of calcination.

Factors upon which the amount of silica incorporated with the zeolite is dependent include temperature, concentration of the silicon compound in the containing medium, the degree to which the zeolite has been dried prior to contact with the silicon compound, and calcination of the zeolite.

After the selectivation sequence, the catalyst is preferably exchanged at least once with $NH_4^+$ ions by immersing the catalyst in a solution containing $NH_4^+$ ions. Most preferably the concentration of $NH_4^+$ ions is approximately 1M. The $NH_4^+$ solution may include various inorganic anions, most preferably $NO_3^-$. Most preferably, the $NH_4^+$ exchange is performed three times.

After the $NH_4^+$ exchange sequence, if any, the catalyst may be subjected to steam treatment at a temperature of from about 100° C. to about 600° C., preferably from about 175° C. to about 325° C.; with from about 1% to about 100% steam, preferably from about 50% to about 100% steam; at a pressure of from about 0.01 psia to about 50 psia; for about two to about twelve hours, preferably from about three to about six hours. The selectivated molecular sieve catalyst, with or without binder, can show improved selectivity upon steaming. Alternatively, excessive steaming can be detrimental to a selectivated catalyst.

The catalyst for use herein can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying, or partially dried and then extruded.

It may be desired to incorporate the crystalline material with another material which is resistant to the temperatures and other conditions employed in the condensation process of this invention. Such materials include active and inactive materials and synthetic or naturally occurring zeolites as well as inorganic materials such as clay, silica, and/or metal oxides such as alumina, magnesia, zirconia, thoria, beryllia, and/or titania. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. Inactive materials suitably serve as diluents to control the amount of conversion so that the products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with zeolite crystals include the montmorillonite and kaolin families which include the subbentonites and the kaolins commonly known as Dixie, McNamee, Georgia, and Florida clays, or others in which the main mineral constituent is halloysite, kaolinite, dickite, nacrite, or anauxite. Such clays can be used in the raw state as originally mined or initially subjected to calcination, acid treatment, or chemical modification. Binders useful for compositing with the zeolite also include inorganic oxides, notably alumina.

In addition to the foregoing materials, the crystals can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia. It may also be advantageous to provide at least a part of the foregoing matrix materials in colloidal form to facilitate extrusion of the bound catalyst components.

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The present process includes converting feedstock comprising aromatic compounds selected from the group consisting of benzene and monocyclic alkyl-substituted benzene of from 7 to 10 carbon atoms to product comprising aromatic compounds which differs from said feedstock, examples of which include isomerizing xylene feedstock components to product enriched in p-xylene with reaction conditions including a temperature from about 230° C. to about 510° C., a pressure of from about 3 atmospheres to about 35 atmospheres, a weight hourly space velocity of from about $0.1\ h^{-1}$ to about $200\ hr^{-1}$ and a hydrogen/hydrocarbon mole ratio of from 0 (no added hydrogen) to about 100; disproportionating toluene to product comprising benzene and xylenes with reaction conditions including a temperature of from about 100° C. to about 760° C., a pressure of from about atmospheric to about 60 atmospheres and a weight hourly space velocity of from about $0.08\ hr^{-1}$ to about 20 $hr^{-1}$; alkylating aromatic hydrocarbons, e.g. benzene and $C_7$ and $C_8$ alkylbenzenes, in the presence of an alkylating agent, e.g. olefins, formaldehyde, alkyl halides and alcohols, with reaction conditions including a temperature of from about 340° C. to about 500° C., a pressure of from about atmospheric to about 200 atmospheres, a weight hourly space velocity of from about $2\ hr^{-1}$ to about $2000\ hr^{-1}$ and an aromatic hydrocarbon/alkylating agent mole ratio of from about 1/1 to about 20/1; and transalkylating aromatic hydrocarbons in the presence of polyalkylaromatic hydrocarbons with reaction conditions including a temperature of from about 340° C. to about 500° C., a pressure of from about atmospheric to about 200 atmospheres, a weight hourly space velocity of from about $10\ hr^{-1}$ to about $1000\ hr^{-1}$ and an aromatic hydrocarbon/polyalkylaromatic hydrocarbon mole ratio of from about 1/1 to about 16/1.

Reaction conditions for the conversion of aromatics as above-detailed include, in general, a temperature of from about 100° C. to about 760° C., a pressure of from about atmospheric to about 200 atmospheres, a weight hourly space velocity of from about $0\ 08\ hr^{-1}$ to about $2000\ hr^1$, and a hydrogen/feedstock aromatic hydrocarbon mole ratio of from 0 (no added hydrogen) to about 100.

Feedstock aromatic compounds converted hereby include individually and in mixture benzene and monocyclic alkyl-substituted benzene of from 7 to 10 carbon atoms having the structure

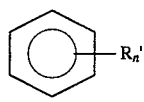

wherein R' is methyl, ethyl or a combination thereof, and n is an integer of from 1 to 4. In other words, the feedstock aromatic compounds may be benzene, benzene containing from 1 to 4 methyl and/or ethyl group substituents, and mixtures thereof. Non-limiting examples of such feedstock compounds include benzene, toluene, xylene, ethylbenzene, mesitylene (1,3,5-trimethylbenzene), durene (1,2,4,5-tetramethylbenzene), pseudocumene (1,2,4-trimethylbenzene) and mixtures thereof.

Other reactant species may be present, such as for alkylation. Alkylating agent species include $C_1$–$C_{24}$ olefins such as ethylene, propylene, dodecylene, as well as formaldehyde, $C_1$–$C_{24}$ alkyl halides and $C_1$–$C_{24}$ alcohols. Numerous other acyclic compounds having at least one reactive alkyl radical may be utilized as alkylating agents.

Products of the present conversion process include alkyl-substituted benzene compounds which differ from feedstock compounds depending upon the conversion desired. The following listing presents non-limiting examples:

| Feedstock Aromatic Compounds Include | Other Reactants Include | Product Aromatic Compounds Include |
|---|---|---|
| Benzene | Ethylene | Ethylbenzene |
| Toluene | Methanol | Xylene Isomers |
| Xylene Isomers e.g., 9:73:18 wt. ratio of para:meta:ortho | — | Different combination of xylene isomers, e.g. 23:57:20 wt. ratio of para:meta:ortho |
| Toluene | — | Benzene and xylenes |
| Benzene | Propylene | Cumene and diisopropylbenzene |
| Toluene | Propylene | Cymene isomers |

Mechanisms of the present process may be isomerization, alkylation, transalkylation and disproportionation. Disproportionation is a special case of transalkylation in which the alkylatable aromatic compound and the transalkylating agent is the same compound, for example, when toluene serves as the doner and acceptor of the transferred methyl group to produce benzene and xylene. Use of the term transalkylation includes the special case of disproportionation.

In order to avoid the need for downstream ethylbenzene removal from the product of, for example, disproportionation in accordance herewith, the level of ethylbenzene by-product is advantageously reduced by incorporating a hydrogenation/dehydrogenation function with the MCM-58 catalyst, such as by addition of a metal compound such as platinum. While platinum is the preferred metal, other metals of Groups IB to VIII of the Periodic Table such as palladium, nickel, copper, cobalt, molybdenum, rhodium, ruthenium, silver, gold, mercury, osmium, iron, zinc, cadmium, and mixtures thereof, may be utilized. The metal may be added by cation exchange, in amounts of from about 0.01% to about 2%, typically about 0.5%. It is desirable that the metal be able to enter the pores of the catalyst. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate or tetraamine platinum(II) chloride. The metallic compound advantageously enters the pores of the catalyst. The catalyst can then be filtered, washed with water and calcined at temperatures of from about 250° C. to about 500° C. It will be appreciated by those skilled in the art that similar considerations apply to processes involving alkylbenzenes other than toluene.

In order to more fully illustrate the nature of the invention and the manner of practicing same, the following examples are presented.

EXAMPLE 1

MCM-58 was synthesized by the procedure of dissolving 16.0 grams of $Al_2(SO_4).18H_2O$ and 22.89 grams of KOH pellets in 406.26 grams of deionized water. After these ingredients were dissolved, 40.65 grams of the organic template benzylquinuclidinium bromide prepared as above was dissolved in the solution. When all of the ingredients were dissolved, this solution was transferred to a one-liter stainless-steel autoclave equipped with a stirrer. Then 144.0 grams of colloidal silica sol (30% $SiO_2$) was mixed into the solution in the autoclave. The mixture was stirred for two minutes to produce a uniform, fluid hydrogel.

After the hydrogel was well stirred, the autoclave was capped and sealed, then 400 psig of inert gas was introduced into the autoclave. Stirring and heating were begun immediately. The crystallization was carried out at 170° C. for two days.

The crystalline product zeolite was filtered, washed with deionized water, than dried on the filter funnel in an air stream under an infrared heat lamp. The dried product powder was proven to be MCM-58 by X-ray diffraction analysis.

EXAMPLE 2

As synthesized zeolite MCM-58 from Example 1 was weighed into a quartz boat, then placed into a Heviduty® tube furnace and sealed with nitrogen gas flowing. The heating of the furnace was begun at 2° C./minute from room temperature to 538° C. When the furnace reached the maximum temperature, the flowing gas was switched to air, and the calcination of the zeolite was continued for 15 hours before termination.

The air calcined sample was $NH_4^+$-exchanged with 1M $NH_4NO_3$ at 80° C. for 6 hours. After $NH_4^+$ exchange, the zeolite was filtered, washed with deionized water, then dried in an air stream on the filter funnel under an infrared heat lamp.

The calcination procedure was repeated on the $NH_4$-MCM-58 sample in the tube furnace in exactly the same manner as described above, except this time the sample was held at the maximum temperature for only 8 hours to convert the zeolite to HMCM-58.

EXAMPLES 3–26

Evaluation of the present process was conducted in an automated unit with on-line product sampling. Catalyst comprised of HMCM-58 from Example 2 was loaded into a stainless steel tube reactor and heated in nitrogen gas to the initial reaction temperature of 420° C. Pure toluene was introduced into the reactor at 420° C., 3 $hr^{-1}$ WHSV, 2 $H_2$/Hydrocarbon mole ratio and 500 psig for Examples 3–24. For evaluation of selectivated HMCM-58, 1 wt. % DOW-550 (dimethylphenylmethyl polysiloxane) was added to the toluene feed for Examples 25 and 26, and reactor temperature and toluene feed rate were varied to change toluene conversion. Results from these examples are presented in Table II.

TABLE II

| Example | 3 | 4 | 5 | 6 | 7 | 8 | 9 | 10 |
|---|---|---|---|---|---|---|---|---|
| TEMP, °C. | 420.30 | 419.70 | 420.20 | 439.90 | 439.90 | 440.30 | 459.70 | 459.70 |
| PRES, psig | 503.20 | 503.90 | 504.10 | 504.20 | 504.10 | 504.40 | 504.20 | 503.20 |
| WHSV, hr$^{-1}$ | 3.04 | 3.04 | 3.04 | 3.04 | 3.04 | 3.04 | 3.04 | 3.04 |
| H$_2$/HC (mol) | 1.99 | 2.00 | 2.00 | 1.99 | 1.98 | 1.99 | 1.99 | 1.99 |
| TOS, hours | 2.95 | 5.98 | 9.03 | 12.08 | 15.12 | 18.17 | 21.22 | 24.25 |
| Product Yields, wt % | | | | | | | | |
| C$_5$- | 6.76 | 5.37 | 4.90 | 8.11 | 8.06 | 7.11 | 11.24 | 10.93 |
| Benzene | 21.26 | 22.21 | 22.54 | 20.98 | 21.44 | 22.06 | 19.73 | 20.99 |
| Toluene | 38.18 | 39.69 | 40.84 | 38.56 | 37.39 | 39.08 | 37.28 | 33.03 |
| Ethylbenzene | 5.96 | 3.61 | 2.99 | 3.27 | 2.47 | 2.38 | 2.33 | 2.19 |
| p-Xylene | 5.13 | 5.16 | 4.67 | 5.00 | 4.93 | 4.81 | 5.05 | 5.22 |
| m-Xylene | 11.48 | 11.45 | 10.51 | 11.03 | 10.93 | 10.67 | 11.13 | 11.62 |
| o-Xylene | 4.67 | 4.84 | 4.48 | 4.65 | 4.94 | 4.77 | 4.68 | 5.26 |
| Ethyltoluene | 2.69 | 2.65 | 2.87 | 2.65 | 2.97 | 2.78 | 2.31 | 2.95 |
| TriMBz | 2.52 | 2.46 | 2.99 | 0.00 | 2.85 | 2.64 | 2.36 | 2.87 |
| DiEbenz | 0.42 | 0.38 | 0.47 | 0.43 | 0.49 | 0.48 | 0.41 | 0.51 |
| DiMeEtBenz | 0.93 | 2.19 | 2.74 | 5.32 | 3.54 | 3.23 | 3.48 | 4.43 |
| TetraMeBenz | 0.00 | 0.00 | 0.00 | 0.00 | 0.00 | 0.00 | 0.00 | 0.00 |
| Other | 0.00 | 0.00 | 0.00 | 0.00 | 0.00 | 0.00 | 0.00 | 0.00 |
| P-Xylene (X) | 24.12 | 24.06 | 23.75 | 24.17 | 23.68 | 23.76 | 24.22 | 23.61 |
| m-Xylene (X) | 53.94 | 53.37 | 53.45 | 53.34 | 52.55 | 52.68 | 53.34 | 52.58 |
| o-Xylene (X) | 21.94 | 22.57 | 22.79 | 22.49 | 23.77 | 23.55 | 22.43 | 23.81 |
| p-Xylene (E) | 102.89 | 102.63 | 101.34 | 103.11 | 101.02 | 101.38 | 103.34 | 100.71 |
| m-Xylene (E) | 103.48 | 102.39 | 102.54 | 102.32 | 100.80 | 101.06 | 102.33 | 100.87 |
| o-Xylene (E) | 89.80 | 92.39 | 93.30 | 92.06 | 97.31 | 96.41 | 91.83 | 97.47 |
| Toluene Conv. | 61.82 | 60.31 | 59.16 | 61.44 | 62.61 | 60.92 | 62.72 | 66.97 |
| Benzene/xylene. (mol) | 1.36 | 1.41 | 1.56 | 1.38 | 1.40 | 1.48 | 1.29 | 1.29 |

| Example | 11 | 12 | 13 | 14 | 15 | 16 | 17 | 18 |
|---|---|---|---|---|---|---|---|---|
| TEMP, °C. | 459.70 | 480.00 | 479.90 | 479.90 | 420.00 | 419.90 | 339.80 | 339.60 |
| PRES, psig | 504.40 | 504.20 | 504.80 | 504.30 | 503.90 | 505.00 | 504.10 | 504.20 |
| WHSV, hr$^{-1}$ | 3.04 | 3.04 | 3.04 | 3.04 | 3.04 | 3.04 | 3.04 | 3.04 |
| H$_2$/HC (mol) | 1.99 | 1.99 | 2.00 | 2.01 | 2.66 | 2.66 | 1.98 | 1.98 |
| TOS, hours | 27.30 | 30.33 | 33.38 | 36.43 | 39.47 | 42.52 | 45.97 | 49.02 |
| Product Yields wt % | | | | | | | | |
| C$_5$- | 10.28 | 15.39 | 14.00 | 13.30 | 1.75 | 1.70 | 0.11 | 0.14 |
| Benzene | 20.41 | 18.76 | 19.68 | 19.47 | 21.85 | 21.86 | 6.55 | 7.24 |
| Toluene | 35.82 | 34.55 | 35.34 | 35.58 | 45.31 | 46.68 | 83.02 | 83.82 |
| Ethylbenzene | 2.28 | 2.21 | 1.99 | 1.95 | 1.23 | 1.48 | 0.53 | 0.42 |
| p-Xylene | 4.90 | 4.67 | 4.57 | 4.67 | 5.33 | 5.50 | 2.05 | 2.04 |
| m-Xylene | 10.86 | 10.28 | 10.30 | 10.41 | 11.84 | 12.16 | 4.16 | 4.07 |
| o-Xylene | 4.72 | 4.58 | 4.57 | 4.58 | 5.13 | 5.19 | 1.58 | 1.50 |
| Ethyltoluene | 3.12 | 1.54 | 1.59 | 2.66 | 1.90 | 1.85 | 0.44 | 0.44 |
| TriMBz | 2.52 | 2.35 | 2.48 | 2.58 | 1.95 | 1.86 | 0.39 | 0.33 |
| DiEbenz | 0.46 | 0.44 | 0.45 | 0.47 | 0.30 | 0.29 | 0.00 | 0.00 |
| DiMeEtBenz | 4.63 | 5.24 | 5.02 | 4.31 | 3.41 | 1.44 | 1.17 | 0.00 |
| TetraMeBenz | 0.00 | 0.00 | 0.00 | 0.00 | 0.00 | 0.00 | 0.00 | 0.00 |
| Other | 0.00 | 0.00 | 0.00 | 0.00 | 0.00 | 0.00 | 0.00 | 0.00 |
| P-Xylene (X) | 23.93 | 23.90 | 23.53 | 23.76 | 23.92 | 24.08 | 26.30 | 26.82 |
| m-Xylene (Y) | 53.03 | 52.65 | 52.97 | 52.92 | 53.10 | 53.21 | 53.42 | 53.48 |
| o-Xylene (X) | 23.04 | 23.44 | 23.50 | 23.31 | 22.98 | 22.71 | 20.27 | 19.70 |
| p-Xylene (E) | 102.09 | 101.98 | 100.38 | 101.39 | 102.03 | 102.73 | 112.22 | 114.41 |
| m-Xylene (E) | 101.72 | 101.01 | 101.61 | 101.52 | 101.86 | 102.08 | 102.48 | 102.58 |
| o-Xylene (E) | 94.32 | 95.95 | 96.20 | 95.42 | 94.07 | 92.94 | 82.99 | 80.66 |
| Toluene Conv. | 64.18 | 65.45 | 64.66 | 64.42 | 54.69 | 53.32 | 16.98 | 16.18 |
| Benzene/xylene (mol) | 1.35 | 1.31 | 1.38 | 1.35 | 1.33 | 1.30 | 1.14 | 1.29 |

| Example | 19 | 20 | 21 | 22 | 23 | 24 | 25 | 26 |
|---|---|---|---|---|---|---|---|---|
| TEMP, °C. | 339.80 | 359.90 | 360.00 | 360.00 | 379.80 | 379.90 | 380.10 | 379.70 |
| PRES, psig | 505.60 | 504.80 | 503.60 | 503.40 | 503.50 | 504.50 | 504.40 | 504.20 |
| WHSV, hr$^{-1}$ | 3.04 | 3.04 | 3.04 | 3.04 | 3.04 | 3.04 | 3.04 | 3.04 |
| H$_2$/HC (mol) | 2.00 | 2.00 | 2.00 | 1.99 | 2.00 | 2.00 | 2.00 | 1.99 |
| TOS, hours | 52.05 | 55.10 | 58.15 | 61.18 | 64.23 | 67.28 | 70.32 | 73.37 |
| Product Yields, wt % | | | | | | | | |
| C$_5$- | 0.12 | 0.31 | 0.29 | 0.31 | 0.68 | 0.45 | 0.52 | 0.44 |
| Benzene | 6.70 | 11.78 | 12.40 | 12.35 | 17.49 | 16.84 | 17.07 | 15.90 |
| Toluene | 84.17 | 72.22 | 72.56 | 71.92 | 59.40 | 61.25 | 59.09 | 63.76 |
| Ethylbenzene | 0.32 | 0.35 | 0.27 | 0.26 | 0.45 | 0.50 | 0.45 | 0.33 |
| p-Xylene | 2.17 | 3.50 | 3.30 | 3.47 | 4.71 | 4.62 | 4.73 | 4.23 |
| m-Xylene | 4.28 | 7.41 | 6.97 | 7.34 | 10.32 | 9.94 | 10.45 | 9.31 |
| o-Xylene | 1.53 | 2.96 | 2.94 | 2.96 | 4.32 | 3.88 | 4.31 | 3.80 |
| Ethyltoluene | 0.38 | 0.69 | 0.57 | 0.65 | 1.13 | 0.91 | 1.11 | 0.54 |

TABLE II-continued

| | | | | | | | | |
|---|---|---|---|---|---|---|---|---|
| TriMBz | 0.33 | 0.62 | 0.50 | 0.55 | 1.13 | 0.97 | 1.16 | 0.85 |
| DiEbenz | 0.00 | 0.09 | 0.00 | 0.00 | 0.14 | 0.18 | 0.16 | 0.12 |
| DiMeEtBenz | 0.00 | 0.08 | 0.19 | 0.19 | 0.23 | 0.47 | 0.93 | 0.72 |
| TetraMeBenz | 0.00 | 0.00 | 0.00 | 0.00 | 0.00 | 0.00 | 0.00 | 0.00 |
| Other | 0.00 | 0.00 | 0.00 | 0.00 | 0.00 | 0.00 | 0.00 | 0.00 |
| P-Xylene (X) | 27.18 | 25.24 | 24.98 | 25.21 | 24.35 | 25.04 | 24.27 | 24.37 |
| m-Xylene (X) | 53.62 | 53.44 | 52.74 | 53.28 | 53.33 | 53.91 | 53.61 | 53.71 |
| o-Xylene (X) | 19.20 | 21.31 | 22.28 | 21.51 | 22.32 | 21.05 | 22.12 | 21.92 |
| p-Xylene (E) | 115.94 | 107.70 | 106.57 | 107.56 | 103.89 | 106.84 | 103.53 | 103.96 |
| m-Xylene (E) | 102.86 | 102.51 | 101.16 | 102.20 | 102.31 | 103.41 | 102.84 | 103.04 |
| o-Xylene (E) | 78.61 | 87.25 | 91.21 | 88.05 | 91.35 | 86.17 | 90.55 | 89.71 |
| Toluene Conv. | 15.83 | 27.78 | 27.44 | 28.08 | 40.60 | 38.75 | 40.91 | 36.24 |
| Benzene/xylene (mol) | 1.14 | 1.15 | 1.28 | 1.22 | 1.23 | 1.24 | 1.19 | 1.25 |

EXAMPLES 27–29

Further evaluation of the present process was conducted in the automated unit of Examples 3–26. Catalyst comprised of HMCM-58 from Example 2 was loaded into the stainless steel tube reactor and heated in nitrogen gas to the initial reaction temperature of 260° C. A mixed feed containing 25 wt. % 1,3-diethylbenzene and 75 wt. % benzene was introduced into the reactor at 260° C., 20 hr$^{-1}$ WHSV, 5 H$_2$/Hydrocarbon mole ratio and 500 psig. Reaction conditions were varied and samples of product were taken and analyzed at 2, 6, and 10 hours on stream. A summary of the reaction conditions and product yield structure is presented in Table III.

TABLE III

| Conditions | | | |
|---|---|---|---|
| Time on Stream, hours | 2 | 6 | 10 |
| Temperature, °C. | 260 | 260 | 260 |
| H$_2$/HC (approx.) | 5 | 10 | 20 |
| Pressure, psig | 500 | 500 | 500 |
| WHSV, hr$^{-1}$ | 20 | 10 | 5 |
| 1,3-DIEB Conversion, Wt % | 50.9 | 62.9 | 88.4 |
| Product Yields, Wt % | | | |
| Benzene | 70.35 | 68.86 | 68.48 |
| Ethylbenzene | 16.13 | 21.32 | 27.34 |
| Toluene | 1.16 | 0.73 | 0.33 |
| C$_{12}$ | 0.14 | 0.00 | 0.00 |
| 1,3-DIEB | 7.77 | 5.88 | 2.49 |
| 1,4-DIEB | 3.47 | 2.61 | 1.10 |
| 11,2-DIEB | 0.80 | 0.60 | 0.25 |

I claim:

1. A process for converting feedstock comprising aromatic compounds to product comprising aromatic compounds which differs from said feedstock which comprises contacting said feedstock at conversion conditions with a catalyst composition comprising a porous crystalline material having the structure of MCM-58.

2. The process of claim 1 wherein said conversion conditions include a temperature of from about 100° C. to about 760° C., a pressure of from about atmospheric to about 200 atmospheres, a weight hourly space velocity of from about 0.08 $^{-1}$ to about 2000 hr$^{-1}$, and a hydrogen/feedstock aromatic hydrocarbon mole ratio of from 0 to about 100.

3. The process of claim 1 wherein said feedstock comprises compounds selected from the group consisting of benzene and monocyclic alkyl-substituted benzene of from 7 to 10 carbon atoms having the structure

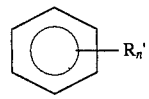

wherein R' is methyl, ethyl or combination thereof, and n is an integer of from 1 to 4.

4. The process of claim 3 wherein said compounds are selected from the group consisting of benzene, toluene, xylene, ethylbenzene, mesitylene, durene, pseudocumene and mixtures thereof.

5. The process of claim 1 wherein said feedstock further comprises an alkylating agent compound selected from the group consisting of C$_1$–C$_{24}$ olefins, formaldehyde, C$_1$–C$_{24}$ alkyl halides and C$_1$–C$_{24}$ alcohols.

6. The process of claim 1 wherein said crystalline material has been treated with one or a combination of monomeric or polymeric selectivating agent compounds, whereby the treated crystalline material has an Alpha Value of from about 150 to about 1200.

7. The process of claim 6 wherein said crystalline material treatment comprises contacting said crystalline material with one or a combination of monomeric or polymeric selectivating agent compounds and then calcining the contacted crystalline material.

8. The process of claim 7 wherein said selectivating agent is a siloxane characterized by the formula:

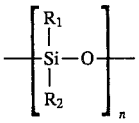

wherein R$_1$ and R$_2$ are independently hydrogen; halogen; hydroxyl; alkyl of from 1 to 10 carbons; halogenated alkyl of from 1 to 10 carbons; aryl, aralkyl, or alkaryl of from 6 to 20 carbons; halogenated aryl, aralkyl, or alkaryl of from 6 to 20 carbons; or mixtures thereof, and n is an integer of from 2 to 1000.

9. The process of claim 7 wherein said selectivating agent is selected from the group consisting of dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone, ethylvinyl silicone, hexamethyl cyclotrisiloxane, octamethyl cyclotetrasiloxane, hexaphenyl cyclotrisiloxane and octaphenyl cyclotetrasiloxane, and mixtures thereof.

10. The process of claim 7 wherein said selectivating agent is a silane characterized by the formula:

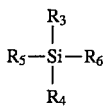

where $R_3$, $R_4$, $R_5$ and $R_6$ are independently selected from the group consisting of hydrogen; hydroxyl; halogen; alkyl of from 1 to 10 carbons; halogenated alkyl of from 1 to 10 carbons; alkoxy of from 1 to 10 carbons; aryl, aralkyl, or alkaryl of from 6 to 20 carbons; halogenated aryl, aralkyl, or alkaryl of from 6 to 20 carbons; organoamine of 3 to 9 carbons; or mixtures thereof.

11. The process of claim 10 wherein said $R_3$, $R_4$, $R_5$, and $R_6$ are independently selected from the group consisting of —$N(CH_3)_3$, —$N(C_2H_5)_3$, —$N(C_3H_7)_3$, and mixtures thereof.

12. The process of claim 7 wherein said contacting is repeated from 2 to 6 times.

13. The process of claim 1 wherein said crystalline material is ion exchanged.

14. The process of claim 1 wherein said crystalline material is steamed at a temperature of from about 100° C. to about 600° C. and a pressure of from about 0.01 psia to about 50 psia.

15. The process of claim 1 wherein said feedstock comprises xylene isomers and said conversion conditions include a temperature of from about 230° C. to about 510° C., a pressure of from about 3 atmospheres to about 35 atmospheres, a weight hourly space velocity of from about $0.1^{-1}$ to about $200^{-1}$ and a hydrogen/hydrocarbon mole ratio of from 0 to about 100.

16. The process of claim 1 wherein said feedstock comprises toluene, said product comprises benzene and xylenes, and said conversion conditions include a temperature of from about 100° C. to about 760° C., a pressure of from about atmospheric to about 60 atmospheres and a weight hourly space velocity of from about $0.08^{-1}$ to about 20 $hr^{-1}$.

17. The process of claim 16 wherein said crystalline material has been treated with one or a combination of monomeric or polymeric selectivating agent compounds, whereby the treated crystalline material has an Alpha Value of from about 150 to about 1200.

18. The process of claim 17 wherein said crystalline material treatment comprises contacting said crystalline material with one or a combination of monomeric or polymeric selectivating agent compounds and then calcining the contacted crystalline material.

19. The process of claim 18 wherein said selectivating agent is a siloxane characterized by the formula:

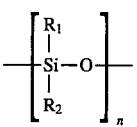

wherein $R_1$ and $R_2$ are independently hydrogen; halogen; hydroxyl; alkyl of from 1 to 10 carbons; halogenated alkyl of from 1 to 10 carbons; aryl, aralkyl, or alkaryl of from 6 to 20 carbons; halogenated aryl, aralkyl, or alkaryl of from 6 to 20 carbons; or mixtures thereof, and n is an integer of from 2 to 1000.

20. The process of claim 18 wherein said selectivating agent is a silane characterized by the formula:

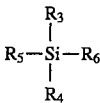

where $R_3$, $R_4$, $R_5$ and $R_6$ are independently selected from the group consisting of hydrogen; hydroxyl; halogen; alkyl of from 1 to 10 carbons; halogenated alkyl of from 1 to 10 carbons; alkoxy of from 1 to 10 carbons; aryl, aralkyl, or alkaryl of from 6 to 20 carbons; halogenated aryl, aralkyl, or alkaryl of from 6 to 20 carbons; organoamine of 3 to 9 carbons; or mixtures thereof.

21. The process of claim 18 wherein said contacting is repeated from 2 to 6 times.

22. The process of claim 5 wherein said conversion conditions include a temperature of from about 340° C. to about 500° C., a pressure of from about atmospheric to about 200 atmospheres, a weight hourly space velocity of from about $2^{-1}$ to about $2000^{-1}$ and a feedstock aromatic hydrocarbon/alkylating agent mole ratio of from about 1/1 to about 20/1.

23. The process of claim 1 wherein said feedstock comprises both aromatic hydrocarbons and polyalkylaromatic hydrocarbons and said conversion conditions include a temperature of from about 340° C. to about 500° C., a pressure of from about atmospheric to about 200 atmospheres, a weight hourly space velocity of from about $10^{-1}$ to about 1000 $hr^{-1}$ and a feedstock aromatic hydrocarbon/polyalkylaromatic hydrocarbon mole ratio of from about 1/1 to about 16/1.

\* \* \* \* \*